(12) United States Patent
Wang et al.

(10) Patent No.: US 9,927,349 B2
(45) Date of Patent: Mar. 27, 2018

(54) METHOD OF PRODUCING THROUGH WIRING SUBSTRATE AND METHOD OF PRODUCING DEVICE

(71) Applicant: CANON KABUSHIKI KAISHA, Tokyo (JP)

(72) Inventors: Shinan Wang, Komae (JP); Yutaka Setomoto, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/379,319

(22) Filed: Dec. 14, 2016

(65) Prior Publication Data

US 2017/0167970 A1 Jun. 15, 2017

(30) Foreign Application Priority Data

Dec. 15, 2015 (JP) .................. 2015-243670

(51) Int. Cl.
| | |
|---|---|
| *G01N 21/00* | (2006.01) |
| *G01N 21/17* | (2006.01) |
| *B06B 1/02* | (2006.01) |
| *B06B 1/06* | (2006.01) |
| *G01H 9/00* | (2006.01) |
| *H05K 1/09* | (2006.01) |
| *H05K 1/11* | (2006.01) |
| *H05K 3/40* | (2006.01) |
| *G01N 29/24* | (2006.01) |
| *H05K 3/00* | (2006.01) |
| *H05K 3/06* | (2006.01) |
| *H05K 3/42* | (2006.01) |

(52) U.S. Cl.
CPC ....... *G01N 21/1702* (2013.01); *B06B 1/0292* (2013.01); *B06B 1/06* (2013.01); *B06B 1/0622* (2013.01); *G01H 9/004* (2013.01); *G01N 29/24* (2013.01); *G01N 29/2406* (2013.01); *G01N 29/2418* (2013.01); *G01N 29/2437* (2013.01); *H05K 1/09* (2013.01); *H05K 1/115* (2013.01); *H05K 3/0041* (2013.01); *H05K 3/4084* (2013.01); *G01N 2021/1706* (2013.01); *H05K 3/06* (2013.01); *H05K 3/42* (2013.01); *H05K 2201/09854* (2013.01); *H05K 2203/025* (2013.01)

(58) Field of Classification Search
CPC .... G01N 29/24; G01N 21/65; G01N 21/1702; G01H 9/004; B06B 1/0292; B06B 1/06; B06B 1/0622; H05K 1/09; H05K 1/115; H05K 3/0041; H05K 3/4084
See application file for complete search history.

(56) References Cited

U.S. PATENT DOCUMENTS 6,646,338 B2 * 11/2003 Hashimoto ......... H01L 23/3114
257/668

FOREIGN PATENT DOCUMENTS

JP       2013-165100 A    8/2013

\* cited by examiner

*Primary Examiner* — Abdullahi Nur
(74) *Attorney, Agent, or Firm* — Canon U.S.A., Inc. IP Division

(57) ABSTRACT

In a method of producing a device in which an element structure is provided on a substrate including a through wiring, a through hole is formed so as to extend from a first surface of the substrate to a second surface of the substrate disposed on an opposite side of the substrate to the first surface, the through wiring is formed by filling the through hole with an electrically conductive material, and the element structure is formed on a first surface side. In the step of forming the through hole, a degree of surface irregularities of an inner wall of the through hole is larger on the first surface side than on a second surface side.

24 Claims, 9 Drawing Sheets

METHOD OF PRODUCING THROUGH WIRING SUBSTRATE AND METHOD OF PRODUCING DEVICE

BACKGROUND

Field of the Disclosure

The present disclosure relates to a through wiring substrate, a device that includes the through wiring substrate, a method of producing the through wiring substrate, a method of producing the device, and so forth.

Description of the Related Art

For reduction of the sizes of devices and advancement of the functions of the devices such as an increase in speed and an increase in the number of functions, through wirings are used. The through wirings allow chips included in such a device to be electrically connected to one another or elements on the top surface of a substrate to be electrically connected to wiring on the bottom surface of the substrate with smallest distances. The through wirings may be formed by a via-first method or a via-last method. With the via-first method, the through wirings are formed before the elements are formed. With the via-last method, the through wirings are formed after the elements have been formed. With the via-first method, a high-quality insulating film can be deposited at a high temperature on the surface of the substrate including inner walls of through holes. This is suitable for a device which needs to have a high dielectric strength. However, when a temperature increasing step is required for the formation of an element structure, it is required to consider effects on the elements due to heat diffusion to the substrate that is the material for forming the through wirings and the difference in thermal expansion between the through wirings and the substrate.

In order to reduce the heat diffusion, a barrier layer may be provided. In order to reduce the difference in thermal expansion, the through wirings can be formed of a material which is similar to the material of the substrate. For example, when the substrate is formed of silicon, the wirings may be formed of phosphorus-doped polysilicon. However, the through wirings formed of polysilicon have a drawback of having a high resistivity. Thus, the through wirings can be formed of metal in the case where the element structure can be formed at a comparatively low temperature. For example, the substrate is formed of silicon and the through wirings are formed of Cu. In this case, the thermal expansion coefficient of Cu is six times larger than that of silicon. Accordingly, when the temperature increases and decreases to form the elements, the through wirings contract and expand or slide relative to the inner wall of the through hole. Due to such a movement, end surfaces of the through wirings project from the surface of the substrate when the temperature increases. This may cause a thin film included in each element to be, for example, deformed, permanently deformed, or to be damaged. Furthermore, when the temperature decreases, such a wiring attempts to return to its original state and draws the thin film. This may cause, in the proximity of the end surface, the thin film to be permanently deformed, damaged, or stress in the thin film may increase. Such permanent deformation of the thin film, damage to the thin film, an increase in stress in the thin film, and so force may cause deficiency of the element and variation of the performance among the elements. In order to reliably obtain the performance of the element, it is possible that the element is not disposed near the through wiring. In this case, however, the degree of integration of elements reduces. In order to reduce or suppress permanent deformation of the thin film, damage to the thin film, or the increase in stress in the thin film, it is required that a relative movement of the through wiring due to a change in temperature be suppressed on the substrate surface side where the element is disposed.

Japanese Patent Laid-Open No. 2013-165100 discloses a technique in which scallops (surface irregularities) is formed in an inner wall of a through hole and the width and depth of the scallops are controlled. When the through wiring is formed in the through hole having such scallops, a structure in which the surface of the through wiring and the inner wall of the through hole are engaged with each other can be produced. Accordingly, the relative movement of the through wiring to the substrate due to the change in temperature can be suppressed.

However, the technique of Japanese Patent Laid-Open No. 2013-165100 has been developed for forming an insulating film and other thin films uniformly on the inner wall of the through hole with a good adhesion property through a via-last method, and the scallops are formed entirely in the through hole. Furthermore, the scallops are formed such that the width and depth of the scallops are smaller on the surface side where the element is disposed than on the surface side where no element is disposed. When the scallops are formed entirely in the through hole, the through wiring is engaged with the inner wall throughout the entire length of the through, and accordingly, restrained. Thus, when the temperature increases or decreases, the through wiring has large stress between the through wiring and the inner wall of the through hole. Due to this stress, the scallops and the thin film formed on the scallops may be eternally deformed or damaged, and accordingly, desired functions are not necessarily performed. Furthermore, the width and depth of the scallops are comparatively small on the surface side where the element is disposed, and accordingly, a force to restrain the through wiring is comparatively small. Thus, the relative movement of the through wiring due to the increase and decrease in temperature may be concentrated on the surface side where the element is disposed. This may increase the effects on the thin film and the like included in the element.

SUMMARY

A method of producing according to an aspect of the present disclosure is a method of producing a device in which an element structure is provided on a substrate including a through wiring. The method includes the steps of forming a through hole that extends from a first surface of the substrate to a second surface of the substrate disposed on an opposite side of the substrate to the first surface, forming the through wiring by filling the through hole with an electrically conductive material, and forming the element structure on a first surface side after the forming of the through wiring. In the step of forming the through hole, a degree of surface irregularities of an inner wall of the through hole is larger on the first surface side than on a second surface side.

A method of producing according to another aspect of the present disclosure is a method of producing a substrate including a through wiring. The method includes the step of forming a through hole that extends from a first surface of the substrate to a second surface of the substrate disposed on an opposite side of the substrate to the first surface and the step of forming the through wiring by filling the through hole with an electrically conductive material. In the step of forming the through hole, a degree of surface irregularities of an inner wall of the through hole is larger on a first surface side than on a second surface side.

A device according to yet another aspect of the present disclosure is a device in which an element structure is provided on a substrate including a through wiring. The device has a through hole that extends from a first surface of the substrate to a second surface of the substrate disposed on an opposite side of the substrate to the first surface. The device includes the through wiring formed of an electrically conductive material with which an inside of the through hole is filled and the element structure provided on a first surface side. A degree of surface irregularities of an inner wall of the through hole is larger on the first surface side than on a second surface side.

A through wiring substrate according to yet another aspect of the present disclosure has a through hole that extends from a first surface of the substrate to a second surface of the substrate disposed on an opposite side of the substrate to the first surface. The through wiring substrate includes a through wiring formed of an electrically conductive material with which an inside of the through hole is filled. A degree of surface irregularities of an inner wall of the through hole is larger on a first surface side than on a second surface side.

With the production methods according to the present disclosure, the degree of the surface irregularities of the inner wall of the through hole is larger, and the surface of the through wiring is more strongly restrained on the first surface side of the substrate. In contrast, the degree of the surface irregularities of the inner wall of the through hole is smaller, and the surface of the through wiring more freely moves on the second surface side of the substrate. Furthermore, with the structure of the device according to the present disclosure, in the step of producing the element structure, permanent deformation of or damage to the thin film or the like near the through wiring due to an increase and a decrease in temperature can be reduced. Accordingly, the element can be disposed in the proximity of the through wiring. This can increase the degree of integration of elements. Furthermore, quality of the thin film formed on the inner wall of the through hole and the upper side of the through hole is high. This can make the device more electrically reliable.

Further features of the present disclosure will become apparent from the following description of exemplary embodiments with reference to the attached drawings.

DESCRIPTION OF THE EMBODIMENTS

According to an aspect of the present disclosure, a through hole that accommodates a through wiring is configured such that the degree of surface irregularities of an inner wall of the through hole is larger on a first surface side than on a second surface side in a substrate. The surface irregularities of the inner wall of the through hole is provided mainly for suppressing a relative movement of the through wiring so as to reduce damage to a thin film and the like included in an element on the first surface side of the substrate on which the element is to be disposed. Meanwhile, the thin film and the like included in the element are mainly damaged by the relative movement of the through wiring in a length direction of the through hole (that is, a direction substantially perpendicular to the first surface and the second surface of the substrate). Accordingly, the surface irregularities of the inner wall of the through hole can be formed so as to effectively suppress the relative movement of the through wiring in the length direction of the through hole on the first surface side of the substrate on which the element is to be disposed. Restrictions on the shape, the size, and so force are not required as long as the surface irregularities of the inner wall of the through hole can perform this function. However, assuming that the above-described function can be performed, a surface irregularity structure that can be easily produced is desired.

Figure 8A:
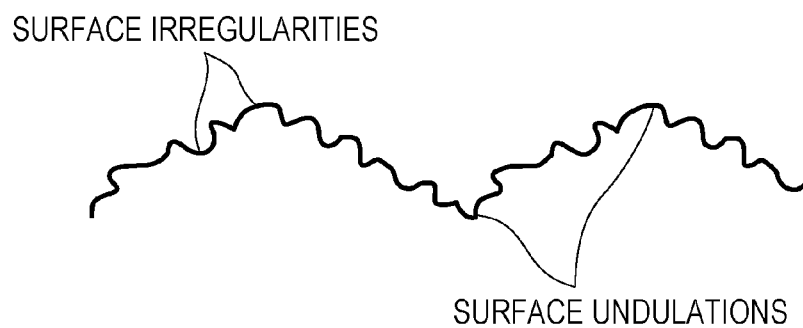
FIGS. 8A and 8B illustrate surface undulations, surface irregularities, a maximum height, and a reference length according to one or more aspects of the present disclosure.
Figure 8B:
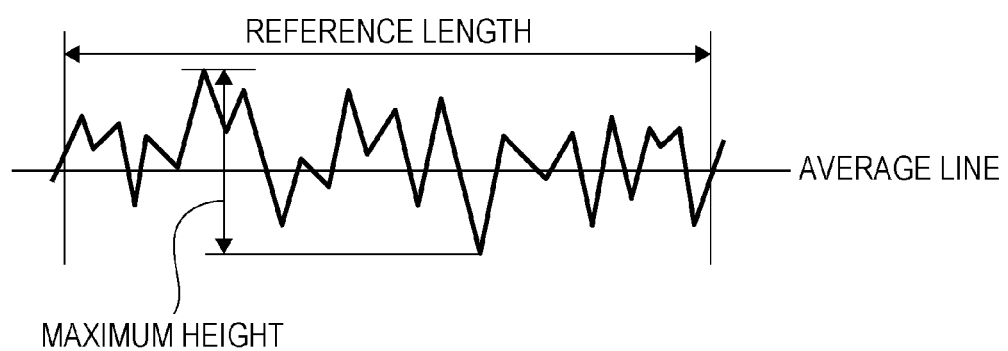

Herein, the surface irregularities of the inner wall of the through hole include either or both of a surface undulating component having a long period and surface roughness component having a short period. As illustrated in FIG. 8A, surface undulations have a long period and surface irregularities have a short period. Furthermore, the surface undulating component and the surface roughness component may be periodically formed or are not necessarily exactly periodically formed. In order to effectively suppress the relative movement of the through wiring in the length direction of the through hole, the surface irregularities of the inner wall of the through hole on the first surface side of the substrate on which the element is to be disposed are formed, for example, such that portions of the surface irregularities having a maximum height are formed periodically (or, at average intervals) in the length direction of the through hole. One of typical examples is a scalloped structure. As illustrated in FIG. 8B, the maximum height here means the sum of the depths as follows: a range of a measured roughness curve is extracted by a reference length in a direction of an average line of the height of the roughness curve; and the sum of the depths from the average line of the extracted range to a highest peak and to a lowest trough is the maximum height. The reference length here is, for example, twice the period (or the average interval) of the surface undulating component. The reference length for the surface roughness component is, for example, 20 μm. That is, when the surface roughness component is discussed, it is assumed that the reference length is 20 μm.

Examples of a device for evaluating the surface irregularities of the inner wall of the through hole include a stylus step profiler and a confocal scanning microscope that includes a laser as the light source. In order to evaluate the surface irregularities of the inner wall of the through hole, for example, the through hole is initially vertically divided in the length direction of the through hole. Then, the shape of the inner wall of the through hole is measured with the confocal scanning microscope or the stylus step profiler.

Embodiments and examples of the present disclosure will be described below with reference to the drawings. It should be understood that the present disclosure is not limited to these embodiments and examples and can be varied and modified in various ways without departing from the scope of the gist of the present disclosure.

First Embodiment

A first embodiment of a method of producing a device according to one or more aspects of the present disclosure is described with reference to FIGS. 1A to 1E. FIGS. 1A to 1E are sectional views illustrating the present embodiment. Although a plurality of through wirings or a plurality of elements are simultaneously formed in a single substrate in typical production of the device, only two through wirings and a single element are illustrated in FIGS. 1A to 1E as appropriate for ease of seeing by simplifying illustration.

Figure 1A:
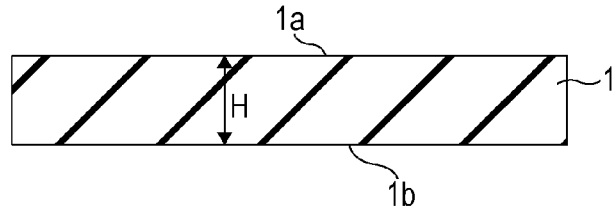
FIGS. 1A to 1E are sectional views illustrating an embodiment of a method of producing a device according to one or more aspects of the present disclosure.

Initially, as illustrated in FIG. 1A, a first substrate 1 is prepared. The first substrate 1 is formed of an insulating material such as glass or a semiconductor material such as Si. The first substrate 1 includes a first surface 1a and a second surface 1b positioned on the opposite side to the first surface. Both the first surface 1a and the second surface 1b of the first substrate 1 are flat and mirror polished. The thickness of the first substrate 1 is, for example, from 50 to 1000 µm.

Figure 1B:
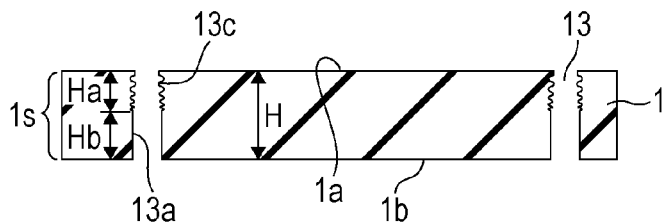

Next, as illustrated in FIG. 1B, through holes 13 are formed in the first substrate 1. The through holes 13 extends from the first surface 1a to the second surface 1b of the first substrate 1, penetrating through the first substrate 1. The number, arrangement, the shape and size of the opening, and so forth of the through holes 13 are defined by a photoresist pattern according to application. The opening of each of the through holes 13 has, for example, a circular shape having a diameter of 20 to 100 µm. The through holes 13 are distributed in, for example, an array in which the period in the lateral direction is 200 µm and the period in the longitudinal direction is 2 mm. After the through holes 13 have been formed, an insulating film or a diffusion preventing film (also referred to as "barrier layer") that prevents metal diffusion is formed on an inner wall 13a of each of the through holes 13 according to need. Both the insulating film and the diffusion preventing film may be formed on the inner wall 13a. At this stage, the degree of surface irregularities 13c of the inner wall 13a of the through hole 13 is made to be larger in a portion Ha on the first surface 1a side than in a portion Hb on the second surface 1b side. Here, "H" represents the thickness of the first substrate 1 and also represents the length of the through hole 13 formed in this first substrate 1.

The surface irregularities 13c of the inner wall 13a of the through hole 13 include either or both of the surface undulating component and the surface roughness component. The surface irregularities 13c of the inner wall 13a of the through hole 13 can be formed so as to effectively suppress the relative movement of a corresponding one of the through wirings in the length direction of the through hole 13 (in a direction denoted by "H") on the first surface 1a side of the first substrate 1 on which an element is to be disposed. The surface undulating component of the surface irregularities 13c of the inner wall 13a of the through hole 13 on the first surface 1a side is formed so as to have, for example, a period (or average interval) having a maximum height in the length direction of the through hole 13. The period (or average interval) of the surface undulating component of the surface irregularities 13c of the inner wall 13a of the through hole 13 is, for example, 5 µm or larger. The period (or average interval) of the surface roughness component of the surface irregularities 13c of the inner wall 13a of the through hole 13 is, for example, 5 µm or smaller. In the portion Ha where the surface irregularities 13c of the inner wall 13a of the through hole 13 are large, the depth (total length) from the first surface 1a is in a range from a length equal to a single period to ten times the period (or ten times the average interval). For example, the period (or average interval) of the surface irregularities 13c is about 5 µm, and more specifically, 50 µm Ha 5 µm. More preferably, Ha is from twice to five times the length of the period of the surface irregularities 13c. For example, the period (or average interval) of the surface irregularities 13c is about 5 µm, and more specifically, 25 µm Ha 10 µm. Preferably, Ha≤1/5H. The lower limit of Ha is such a length with which the effect is sufficiently produced. When the upper limit is increased, expansion and contraction of the through wiring is excessively restricted. This causes stress between the through wiring and the inner wall 13a of the through hole 13 to excessively increase, and as a result, the insulating film or the like existing on the surface of the inner wall 13a of the through hole 13 may be damaged. Here, when the length of the through hole 13 is H, the degree of the surface irregularities 13c of the inner wall 13a of the through hole 13 can be larger in a region having the length of 1/5H on the first surface 1a side than that in the other region on the second surface 1b side than this 1/5H region.

The maximum height of the surface undulating component of the surface irregularities 13c of the inner wall 13a of the through hole 13 is, for example, 2 to 50 µm. The maximum height of the surface roughness component of the surface irregularities 13c of the inner wall 13a of the through hole 13 is, for example, 0.1 to 5 µm. The maximum height of the surface irregularities 13c of the inner wall of the through hole 13 in a portion Hb on the second surface 1b side of the first substrate 1 is smaller than that in the portion Ha on the first surface 1a side, and preferably, 2 µm or smaller. More preferably, the maximum height of the surface irregularities 13c of the inner wall 13a of the through hole 13 in a portion Hb on the second surface 1b side of the first substrate 1 is 0.5 µm or smaller.

Also, in order to prevent an electric field from concentrating more than a standard in the surface irregularities 13c of the inner wall 13a of the through hole 13, the envelope of the peaks (or troughs) of the surface irregularities 13c can be smooth. For example, the diameter of curvature of the envelope of the peaks (or troughs) of the surface irregularities 13c is made not to be smaller than the maximum height of the surface roughness component according to the above-described need. Accordingly, the inner wall 13a of the through hole 13 is smoothed according to need.

The surface irregularities 13c of the inner wall 13a of the through hole 13 can be formed at the same time as processing of the through hole 13. Alternatively, the surface irregularities 13c can be formed by processing the surface of the inner wall 13a of the through hole 13 after the through hole 13 has been formed. Alternatively, the shape of irregularities can be formed by forming a substance having a good adhesion property on the inner wall 13a of the through hole 13 after the through hole 13 has been formed. In this case, the substance for the shape of irregularities can be formed after the insulating film or the barrier layer has been formed on the inner wall 13a of the through hole 13 according to need. Furthermore, the shape of irregularities can be formed by forming a substance having a good adhesion property on the inner wall 13a of the through hole 13 after the through hole 13 has been formed, and then processing the substance. Also in this case, the irregularities can be formed in the substance for the shape of irregularities after the insulating film or the barrier layer has been formed on the inner wall 13a of the through hole 13 according to need. In order to form the surface irregularities 13c of the inner wall 13a of the through hole 13 at the same time as the processing of the through hole 13, for example, the conditions for processing the through hole 13 are changed according to need. The processing conditions subjected to changes vary depending on methods of processing. This will be described in a little more detail with reference to FIG. 3B of a first example later.

More specific examples of the surface irregularities 13c of the inner wall 13a of the through hole 13 include a scalloped structure. That is, a scalloped structure having a larger maximum height in the portion Ha than that in the portion Hb is formed in the inner wall 13a of the through hole 13. With the surface irregularities 13c of the inner wall 13a formed as described above, in a step of forming an element structure 30 of FIG. 1D, the surfaces of through wirings 2 can be strongly constrained on the first surface 1a side of the first substrate 1 where the element is to be disposed, and accordingly, the amount of protrusion of the end surface of each of the through wirings 2 can be reduced. In contrast, the surface of the through wiring 2 can more freely move on the second surface 1b side of the first substrate 1 where the degree of the surface irregularities 13c of the inner wall 13a of the through hole 13 is smaller. Thus, stress between the surface of the through wiring 2 and the inner wall 13a of the through hole 13 is effectively relieved. This can reduce damage to the inner wall 13a of the through hole 13 including the surface irregularities 13c. The first substrate 1 that has the through holes 13 in which the surface irregularities 13c of the inner walls 13a as described above are formed is referred to as a through hole substrate 1s.

Figure 1C:
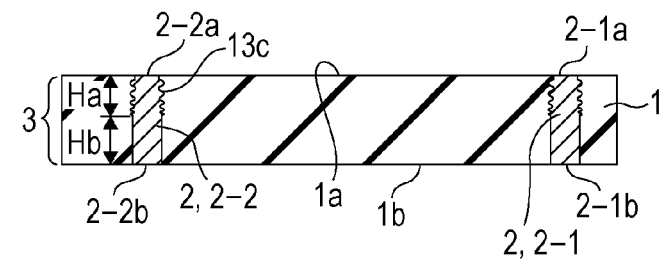

Next, as illustrated in FIG. 1C, the through wirings 2 (including the through wirings 2-1 and 2-2) are formed in the through holes 13 (see FIG. 1B) of the through hole substrate 1s. The through wirings 2 are formed of an electrically conductive material. The through wirings 2 are formed by, for example, Cu electroplating and chemical mechanical polishing (CMP).

In the electroplating step, the first surface 1a of the substrate and a seed film formed on a seed substrate are bonded to each other with a bonding substance interposed therebetween, and the bonding substance at a bottom portion of the through holes 13 is removed so as to expose the seed film. The insides of the through holes 13 are filled with the electrically conductive material by electroplating starting from this exposed seed film. The side surfaces of the through wirings 2 are formed so as to be engaged with the surface irregularities 13c of the inner walls 13a of the through holes 13. End surfaces 2-1a and 2-2a of the through wirings 2 on one side are planarized, so that the levels of the end surfaces 2-1a and 2-2a are the same as substantially the same as that of the first surface 1a of the substrate 1. Also, end surfaces 2-1b and 2-2b of the through wirings 2 on the other side are planarized, so that the levels of the end surfaces 2-1b and 2-2b are the same or substantially the same as that of the second surface 1b of the substrate 1.

Figure 1D:
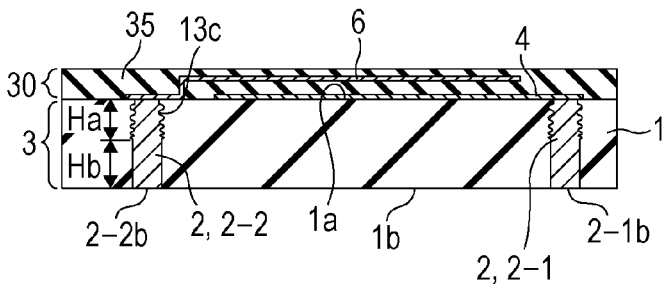

Next, as illustrated in FIG. 1D, the element structure 30 is formed on the first surface 1a of the first substrate 1. The element structure 30 includes electrodes (including a first electrode 4 and a second electrode 6) and miscellaneous parts 35. The electrodes are formed of metal. The first electrode 4 and the second electrode 6 are respectively electrically connected to the end surfaces 2-1a and 2-2a (see FIG. 1C) of the through wirings 2. The element structure 30 is, for example, one of a variety of micro electromechanical system (MEMS) elements. More specifically, the element structure 30 is a capacitive micromachined ultrasonic transducer (CMUT). The configuration of the element structure 30 is designed in accordance with the specification of the device. For example, the element structure 30 is a CMUT and includes the first electrode 4, the second electrode 6 separated from the first electrode 4 with a gap formed therebetween, and a vibrating film that includes insulating films disposed on the upper and lower sides of the second electrode 6 and is supported such that the vibrating film can vibrate. In order to form an element, application of heat up to some hundred degrees centigrade may be required. Due to an increase and a decrease in temperature, the through wirings 2 move relative to the inner walls 13a of the through holes 13 (see FIG. 1B) in proportion to the amount of change in temperature.

The degree of the surface irregularities 13c (see FIG. 1B) of the inner walls 13a of the through holes 13 is larger and the surfaces of the through wirings 2 are more strongly restrained in the portions Ha on the first surface 1a side of the substrate where the element structure 30 is disposed. In contrast, the degree of the surface irregularities 13c of the inner walls 13a of the through holes 13 is smaller and the surfaces of the through wirings 2 are less restrained in the portions Hb on the second surface 1b side of the substrate where no element structure 30 is disposed. Thus, the relative movement of the through wirings 2 due to the increase and decrease in temperature is small on the first surface 1a side where the element structure 30 is disposed and concentrated on the second surface 1b side where no element structure 30 is disposed. As a result, the amounts of projection of the end surfaces (including end surfaces 2-1a and 2-2a; see FIG. 1C) of the through wirings 2 to the first surface 1a side are small on the first surface 1a side. This reduces the likelihood of thin films included in the element (including the first electrode 4, the second electrode 6, and the miscellaneous parts 35) being permanently deformed or damaged. Furthermore, a good uniformity of the film thickness and membrane stress of the thin films included in the element is achieved even in regions proximity to the end surfaces 2-1a and 2-2a of the through wirings 2. In contrast, the relative movement of the end surfaces including end surfaces 2-1b and 2-2b on the second surface 1b side of the through wirings 2 is large. However, since thin films have not yet been formed on the surfaces, there arises no problem. Furthermore, stress between the through wirings 2 and the inner walls 13a of the through holes 13 is relieved on the second surface 1b side. This reduces the likelihood of the surface irregularities 13c of the inner walls 13a of the through holes 13 being damaged on the first surface 1a side.

Figure 1E:
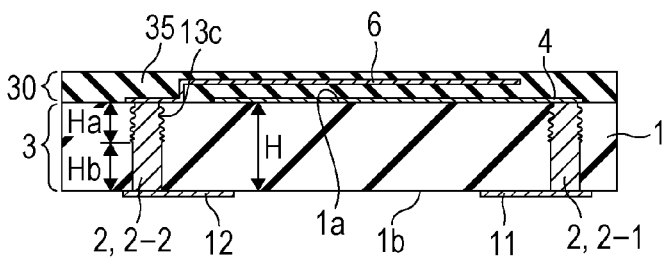

Next, as illustrated in FIG. 1E, electrode pads (including electrode pads 11 and 12) are formed on the second surface 1b side of the first substrate 1. The electrode pads 11 and 12 are respectively connected to the end surfaces 2-1b and 2-2b (see FIG. 1D) of the through wirings 2. The electrode pads 11 and 12 are mainly formed of metal. For example, the electrode pads 11 and 12 each include a Ti thin film serving as an adhesion layer and an Al thin film formed on the Ti thin film. A method of forming the electrode pads 11 and 12 includes, for example, a method that includes sputter deposition of metal, formation of an etching mask including photolithography, and etching of metal. In these steps, the maximum temperature of the substrate is about 100° C., and accordingly, the movement of the through wirings 2 relative to the inner walls 13a of the through holes 13 (see FIG. 1B) due to the increase and decrease in temperature is small. This reduces permanent deformation of or damage to the thin metal films included in the electrode pads 11 and 12. Furthermore, the malleability of the metal thin films is comparatively high. This further reduces permanent deformation of or damage to the electrode pads 11 and 12 due to stress. Furthermore, with the increase and decrease in temperature in these steps, it is unlikely to permanently deform or damage the thin films included in the element structure 30 (including the first electrode 4, the second electrode 6, and the miscellaneous parts 35). Furthermore, with the increase and decrease in temperature in these steps, it is unlikely to damage the surface irregularities 13c of the inner walls 13a of the through holes 13 on the first surface 1a side.

Next, although it is not illustrated, the device (including the element structure 30, a through wiring substrate 3, and electrode pads 11 and 12) having been produced in steps of FIGS. 1A to 1E is connected to a control circuit through the electrode pads 11 and 12. Examples of a connection method include direct coupling by metal, coupling through bumps, compression bonding using anisotropic conductive film (ACF), wire bonding, and so forth.

With the above-described method of production, the device of FIG. 1E can be produced. With this method of production, while the temperature is increased and decreased for forming the element structure, the amounts of projection of the end surfaces 2-1a and 2-2a of the through wirings 2 on the first surface 1a side where the element is to be disposed are reduced. This reduces the likelihood of the thin films or the like disposed around the end surfaces and included in the element being permanently deformed or damaged. As a result, uniformity of the film thickness and membrane stress of the thin films included in the element is good also in the regions proximity to the through wirings 2. Furthermore, the likelihood of the thin film or the like formed on the inner walls 13a of the through holes 13 or on the upper side of the through holes 13 being permanently deformed or damaged is reduced. This makes the device more electrically reliable. Furthermore, in a via-first method, while the temperature is increased and decreased for forming the element, the relative movement of the through wirings 2 is small on the first surface 1a side where the element is to be disposed and concentrated on the second surface 1b side where no element is to be disposed. Accordingly, even when the element is disposed in the proximity of the through wirings 2, variation in performance or degradation of the element is reduced. This increases the degree of integration of elements.

The device according to the present disclosure may be any of optical devices and electronic devices including semiconductor devices and MEMS devices.

Second Embodiment

Figure 2:
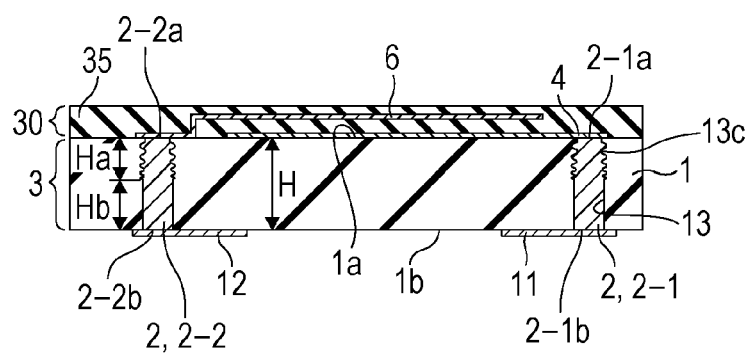
FIG. 2 is a sectional view illustrating an embodiment of the structure of the device according to one or more aspects of the present disclosure.

An embodiment of a structure of the device according to one or more aspects of the present disclosure is described with reference to FIG. 2. FIG. 2 is a sectional view illustrating a second embodiment. Typically, a plurality of through wirings or a plurality of elements are formed in a single device. However, only two through wirings and a single element are illustrated in FIG. 2 for ease of seeing by simplifying illustration.

As illustrated in FIG. 2, the device according to the present embodiment includes the through wiring substrate 3, the element structure 30, and the electrode pads 11 and 12. The through wiring substrate 3 includes the first substrate 1, the through holes 13 that extend from the first surface 1a to the second surface 1b of the first substrate 1, the second surface 1b being the opposite surface to the first surface 1a, and the through wirings 2 (including the through wirings 2-1 and 2-2) formed of the electrically conductive material with which the insides of the through holes 13 are filled. The degree of the surface irregularities 13c of the inner walls of the through holes 13 is larger in the portions Ha on the first surface side than in the portions Hb on the second surface side. The element structure 30 includes the first electrode 4, the second electrode 6, and the miscellaneous parts 35. The element structure 30 is formed on the first surface 1a side of the first substrate 1. The first electrode 4 and the second electrode 6 of the element structure 30 are respectively electrically connected to the end surfaces 2-1a and 2-2a of the through wirings 2-1 and 2-2. The electrode pads 11 and 12 are formed on the second surface 1b side of the first substrate 1. The electrode pads 11 and 12 are respectively electrically connected to the end surfaces 2-1b and 2-2b of the through wirings 2-1 and 2-2. Furthermore, although it is not illustrated, the control circuit may be connected to the device of FIG. 2 through the electrode pads 11 and 12 by any one of the following methods: direct coupling by metal, coupling through bumps, ACF compression bonding, wire bonding, and so forth.

The first substrate 1 is selected in accordance with the performance of the device. The first substrate 1 is formed of an insulating material such as glass or a semiconductor material such as Si. The thickness of the first substrate 1 is, for example, from 100 to 1000 μm. According to need of electrical insulation, an insulating film may be provided on the surfaces of the first substrate 1 including the first surface 1a, the second surface 1b, and the inner walls of the through holes 13 that accommodate the through wirings 2.

The through holes 13 extend from the first surface 1a to the second surface 1b of the first substrate 1, penetrating through the first substrate 1. The number, arrangement, the shape and size of the opening, and so forth of the through holes 13 are determined in the design according to application. The opening of each of the through holes 13 has, for example, a circular shape having a diameter of 20 to 100 μm. The through holes 13 are distributed in, for example, an array in which the period in the lateral direction is 200 μm and the period in the longitudinal direction is 2 mm. An insulating film and a barrier layer may be formed on the inner wall of each of the the through holes 13 according to need. The degree of the surface irregularities 13c of the inner wall (including the insulating film and the barrier layer if these are provided) of the through hole 13 is larger in the portion Ha on the first surface 1a side than in the portion Hb on the second surface 1b side. The depth of the portion Ha from the first surface 1a is preferably 50 μm or smaller. When the thickness H of the first substrate 1 is 250 μm or smaller, it is preferable that Ha do not exceed 1/5 of H (that is, Ha≤1/5H). The surface irregularities 13c of the inner wall of the through hole 13 include either or both of the surface undulating component and the surface roughness component. The period (or average interval) and the maximum height of the surface undulating component of the surface irregularities 13c of the inner wall of the through hole 13 are, for example, 5 μm or larger and from 2 to 50 μm, respectively. The period (or average interval) and the maximum height of the surface roughness component of the surface irregularities 13c of the inner wall of the through hole 13 are, for example, 5 μm or smaller and from 0.1 to 5 μm, respectively. Furthermore, the envelope of the peaks (or troughs) of the surface irregularities 13c is smooth. For example, the diameter of curvature of the envelope of the peaks (or troughs) of the surface irregularities 13c is made not to be smaller than the maximum height of the surface roughness component. More specific examples of the surface irregularities 13c of the inner wall of the through hole 13 include a scalloped structure. That is, the portion Ha of the inner wall of the through hole 13 has a scalloped structure having a larger maximum height than that of the portion Hb of the inner wall of the through hole 13.

The through wirings 2 are formed of an electrically conductive material. The through wirings 2 are, for example, formed of a material including metal. Preferably, the through wirings 2 are formed of a highly conductive material (Cu, a Cu alloy, or the like) including Cu as a main material (herein, this means that most of the material is made up of Cu).

The element structure 30 is, for example, any of a variety of MEMS elements. More specifically, the element structure 30 is, for example, a CMUT or a piezoelectric transducer. The element structure 30 is designed in accordance with the specification of the device. For example, the element structure 30 is a CMUT and includes the first electrode 4, the second electrode 6 separated from the first electrode 4 with a gap formed therebetween, and the vibrating film that includes insulating films disposed on the upper and lower sides of the second electrode 6 and is supported such that the vibrating film can vibrate. The electrodes (including the first electrode 4 and the second electrode 6) of the element structure 30 are formed of a metal material.

The electrode pads (including the electrode pads 11 and 12) are formed of metal. For example, the electrode pads 11 and 12 each include a Ti thin film serving as an adhesion layer and an Al thin film formed on the Ti thin film.

With the structure of the device according to the present embodiment, in steps for producing the element, permanent deformation of or damage to the thin films or the like near the through wirings 2 due to an increase and a decrease in temperature is reduced. Accordingly, the element can be disposed in the proximity of the through wirings 2. This increases the degree of integration of elements. Furthermore, quality of the thin films formed on the inner walls of the through holes 13 and on the upper side of the through holes 13 is high. This makes the device more electrically reliable.

More specific examples will be described below.

First Example

A first example of the method of producing the device according to one or more aspects of the present disclosure is described with reference to sectional views of FIGS. 3A to 3F. For ease of seeing, only two through wirings and a single element are illustrated as appropriate also in FIGS. 3A to 3F.

Figure 3A:
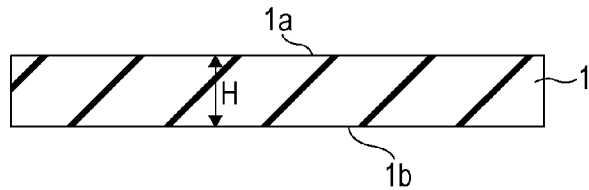
FIGS. 3A to 3F are sectional views illustrating a first example of a method of producing the device according to one or more aspects of the present disclosure.

Initially, as illustrated in FIG. 3A, the first substrate 1 is prepared. As the first substrate 1, an Si substrate is used. The first substrate 1 includes the first surface 1a and the second surface 1b. These two surfaces are mirror polished so as to have a surface roughness of Ra≤2 nm. The resistivity of the first substrate 1 is about 0.01 Ω·cm. The thickness H of the first substrate 1 is about 300 µm.

Figure 3B:
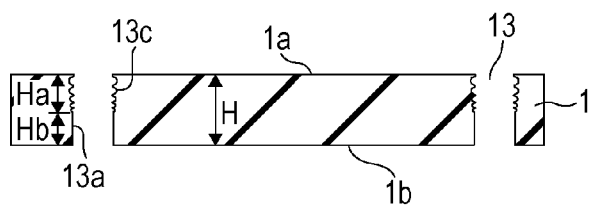

Next, as illustrated in FIG. 3B, the through holes 13 are formed so as to extend from the first surface 1a to the second surface 1b of the first substrate 1. The through holes 13 each have a substantially cylindrical shape. The diameter of the openings in the first surface 1a and the second surface 1b of the first substrate 1 is about 50 µm. The through holes 13 are arranged with a period of 400 µm in the first substrate 1.

Processing of the through holes 13 are performed by using a deep reactive ion etching (RIE) technique for Si for which a Bosch process is adopted. When performing the RIE process, the processing conditions are adjusted so as to form a scalloped structure as the surface irregularities 13c in the inner wall 13a of each of the through hole 13 in the portion Ha on the first surface 1a side. The processing conditions mentioned here include a time period for etching step, a time period for protective film formation, a source power for etching, a bias power for etching, and so forth. The portion Ha is about 18 µm, an average interval of the scallops in the portion Ha is about 6 µm, and the maximum height of the scallops is about 5 µm. Scallops in the inner wall 13a of the through hole 13 in the portion Hb on the second surface 1b side are made to have a maximum height of 0.5 µm or smaller. After performing the RIE process, the inner wall 13a of the through hole 13 is smoothed so that the inner wall 13a of the through hole 13 where projections including the peaks of the scallops are smoothed. The smoothing is performed by thermal oxidation of the surface of the first substrate 1 formed of Si and removal of a thermal oxidation film from the surface of the first substrate 1. The smoothing is performed so that, when an insulating film 14 of FIG. 3C has been formed, the diameter of curvature of the envelope of the peaks (or troughs) of the surface irregularities 13c in the inner wall 13a of the through hole including the insulating film 14 is 5 µm or larger.

Figure 3C:
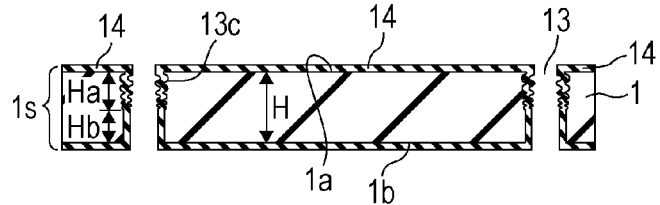

Next, as illustrated in FIG. 3C, the insulating film 14 is formed on the surfaces of the first substrate 1 including the first surface 1a, the second surface 1b, and the inner walls 13a (see FIG. 3B) of the through holes 13. As the insulating film 14, a thermal oxidation film formed of Si having a thickness of about 1 µm is used. The first substrate 1 having the through holes 13 formed in the step of FIG. 3B is subjected to a heating process at about 1000° C. in an oxygen atmosphere so as to form the Si thermal oxidation film. As described above, the diameter of curvature of the envelope of the peaks (or troughs) of the surface irregularities 13c in the inner walls 13a of the through holes 13 including the insulating film 14 is 5 µm or larger.

Figure 3D:
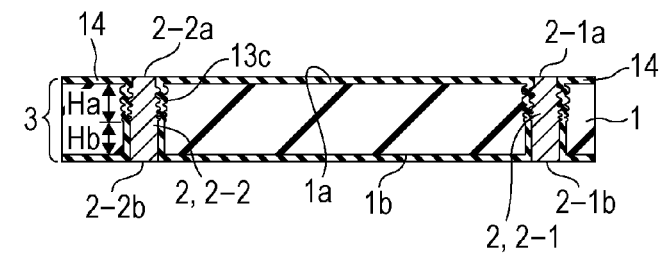

Next, as illustrated in FIG. 3D, the through wirings 2 (including the through wirings 2-1 and 2-2) are formed in the through holes 13 (see FIG. 3C). As a method of forming the through wirings 2, the insides of the through holes 13 (see FIG. 3C) are filled with Cu by electroplating, and then, end surfaces of Cu is planarized by the CMP process. After the planarization, on the first surface 1a side of the substrate, the levels of the end surfaces 2-1a and 2-2a of the through wirings 2 are the same or substantially the same as that of the surface of the thermal oxidation film 14 on the first surface 1a side. Furthermore, on the second surface 1b side, the levels of the end surfaces 2-1b and 2-2b of the through wirings 2 are the same or substantially the same as that of the surface of the thermal oxidation film 14 on the second surface 1b side.

Figure 3E:
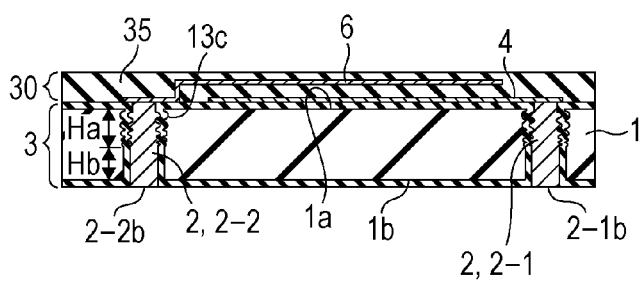

Next, as illustrated in FIG. 3E, the element structure 30 is formed on the first surface 1a of the through hole substrate 1s (the same surface as that of the first surface 1a of the first substrate 1). The element structure 30 includes the electrodes (including the first electrode 4 and the second electrode 6) and the miscellaneous parts 35. The electrodes are formed of metal. The first electrode 4 and the second electrode 6 are respectively electrically connected to the end surfaces 2-1a and 2-2a (see FIG. 3D) of the through wirings 2. The element structure 30 is, for example, a CMUT. The maximum temperature of the substrate is about 300° C. in the step of forming the element structure 30.

Figure 3F:
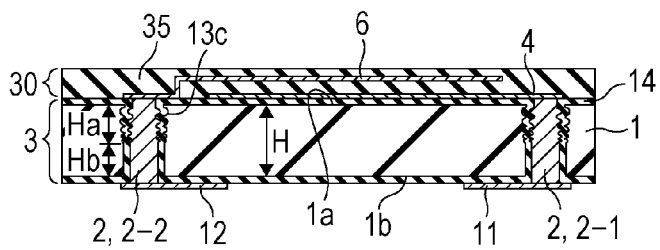

Next, as illustrated in FIG. 3F, the electrode pads (including the electrode pads 11 and 12) electrically connected to the end surfaces (including the end surfaces 2-1b and 2-2b; see FIG. 3E) of the through wirings 2 are formed on the second surface 1b side. The electrode pads 11 and 12 are respectively connected to the end surfaces 2-1b and 2-2b of the through wirings 2. The electrode pads 11 and 12 each include a Ti thin film having a thickness of 50 nm and an Al thin film having a thickness of 500 nm formed on the Ti thin film. The electrode pads 11 and 12 are formed by sputter deposition featuring good coatability. The maximum temperature of the substrate is about 100° C. in the step of forming the electrode pads 11 and 12.

Next, although it is not illustrated, the device (including the element structure 30, the through hole substrate 1s, and the electrode pads 11 and 12) having been produced in the steps of FIGS. 3A to 3F is connected to a control circuit through the electrode pads 11 and 12 by the ACF compression bonding method. With the first example, the effects that are the same or similar to those obtained with the production method of the first embodiment can be obtained.

Second Example

A second example of the device according to one or more aspects of the present disclosure is described with reference to sectional views of FIG. 4. For ease of seeing, only two through wirings and a single element are illustrated also in FIG. 4.

Figure 4:
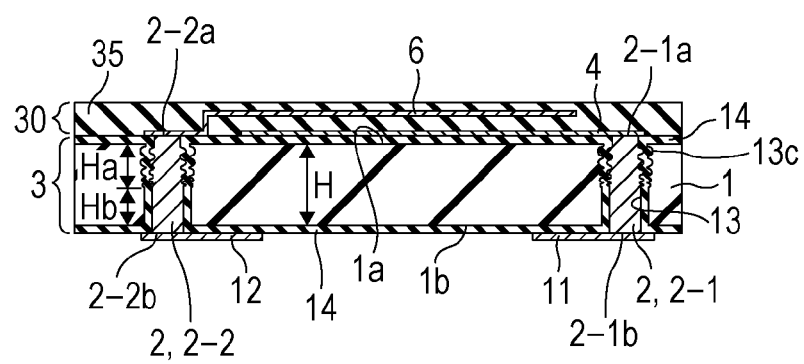
FIG. 4 is a sectional view illustrating an example of the structure of the device according to one or more aspects of the present disclosure.

As illustrated in FIG. 4, the device according to the present example includes the through wiring substrate 3, the element structure 30, and the electrode pads 11 and 12. The through wiring substrate 3 includes the first substrate 1, the through holes 13 that extend from the first surface 1a to the second surface 1b of the first substrate 1, the insulating film 14 formed on the surfaces of the first substrate 1 including the inner walls of the through holes 13, and the through wirings 2 (including the through wirings 2-1 and 2-2) formed of the electrically conductive material with which the insides of the through holes 13 are filled. The element structure 30 includes the first electrode 4, the second electrode 6, and the miscellaneous parts 35. The element structure 30 is formed on the first surface 1a side of the first substrate 1. The first electrode 4 and the second electrode 6 of the element structure 30 are respectively electrically connected to the end surfaces 2-1a and 2-2a of the through wirings 2-1 and 2-2. The electrode pads 11 and 12 are formed on the second surface 1b side of the first substrate 1. The electrode pads 11 and 12 are respectively electrically connected to the end surfaces 2-1b and 2-2b of the through wirings 2-1 and 2-2.

The first substrate 1 is an Si substrate. The first substrate 1 includes the first surface 1a and the second surface 1b. These two surfaces are mirror polished so as to have a surface roughness of Ra≤2 nm. The resistivity of the first substrate 1 is about 0.01 Ω·cm. The thickness H of the first substrate 1 is about 300 μm. The through holes 13 each have a diameter of 50 μm. The through holes 13 are arranged with the period in the lateral direction set to 400 μm and the period in the longitudinal direction set to 2 mm. As the insulating film, the thermal oxidation film 14 formed of Si having a thickness of about 1 μm is formed in the inner wall of each of the through holes 13. Furthermore, the scalloped structure serving as the surface irregularities 13c is formed in each of the inner walls in the portion Ha on the first surface 1a side. The total length of the portion Ha is about 18 μm, an average interval of the scallops in the portion Ha is about 6 μm, and the maximum height of the scallops is about 5 μm. The scallops in the inner wall of the through hole 13 in the portion Hb on the second surface 1b side have a maximum height of 0.5 μm or smaller. The diameter of curvature of the envelope of the peaks (or troughs) of the surface irregularities 13c in the inner wall of the through hole 13 including the insulating film 14 is 5 μm or larger. The through wirings 2 are mainly formed of Cu.

The element structure 30 is a CMUT. The CMUT includes the first electrode 4, the second electrode 6 separated from the first electrode 4 with a gap formed therebetween, and the vibrating film that includes the insulating films disposed on the upper and lower sides of the second electrode 6 and is supported such that the vibrating film can vibrate. The electrode pads (including electrode pads 11 and 12) each include the Ti thin film having a thickness of 50 nm and the Al thin film having a thickness of 500 nm formed on the Ti thin film. Furthermore, although it is not illustrated, the control circuit is connected to the device of FIG. 4 through the electrode pads 11 and 12 by the ACF compression bonding method. With the second example, the effects that are the same or similar to those obtained with the device of the second embodiment can be obtained.

Third Example

Figure 5:
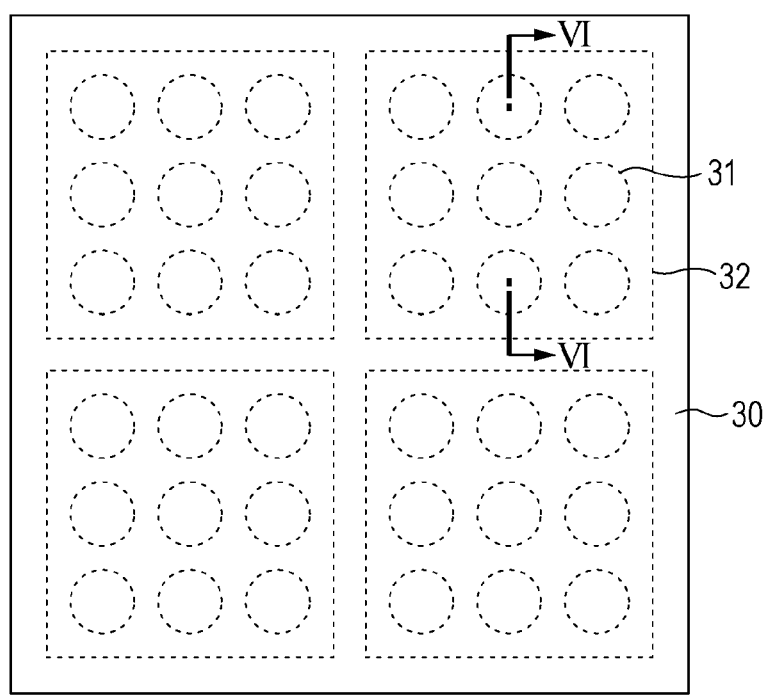
FIG. 5 is a plan view illustrating a third example of the method of producing the device according to one or more aspects of the present disclosure.

A third example of the method of producing the device according to one or more aspects of the present disclosure is described with reference to a plan view of FIG. 5 and sectional views of FIGS. 6A to 6K. An example of the method of producing the CMUT on the through wiring substrate by a via-first method is described according to the present example.

The CMUT is a capacitive transducer that can transmit and receive an acoustic wave such as an ultrasonic wave using vibration of a vibrating film. In particular, with the CMUT, good wide-band characteristics can be easily obtained in liquid. In practical use, as illustrated in the plan view of FIG. 5, a single CMUT device has the following configuration so as to realize desired performance: the element structure 30 includes a plurality of element portions 32 arranged on the substrate, and each of the element portions 32 includes a plurality of vibrating films (also referred to as "cells") 31 arranged in a two-dimensional array. In order to independently control each of the element portions 32, wiring portions are formed so as to correspond to the respective element portions 32. The structure of a cell of FIGS. 6A to 6K for description of the production process is taken along line VI-VI of FIG. 5. For simplicity, only a single cell (a single vibrating film) of the CMUT and a pair of the through wirings are illustrated as appropriate in FIGS. 6A to 6K.

Figure 6A:
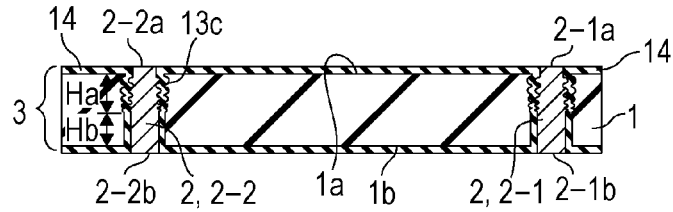
FIGS. 6A to 6K are sectional views illustrating the third example of the method of producing the device according to one or more aspects of the present disclosure.
Figure 6B:
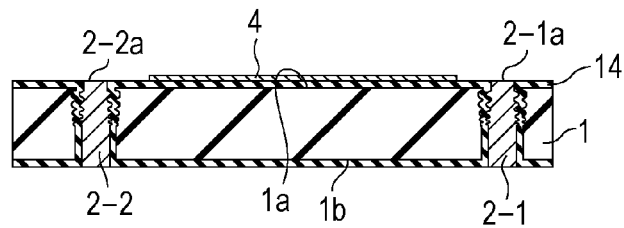
Figure 6C:
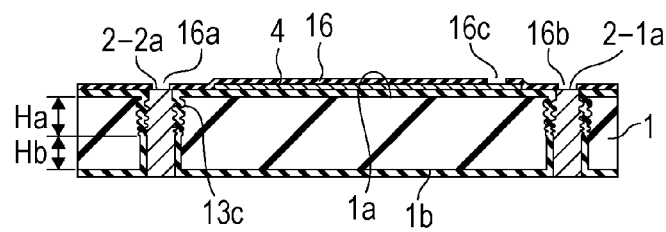
Figure 6D:
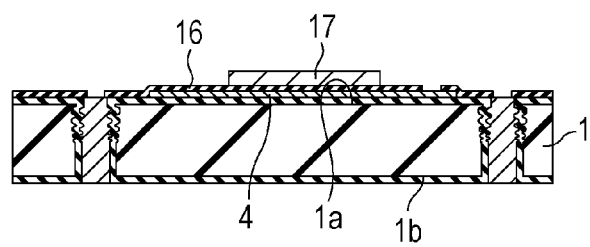
Figure 6E:
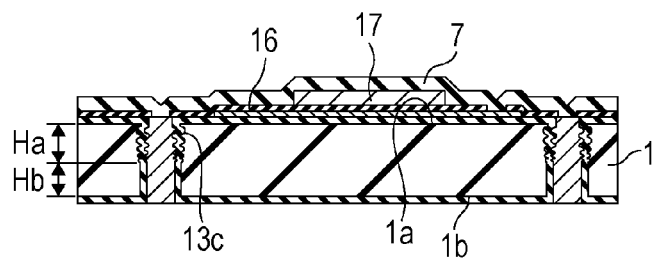
Figure 6F:
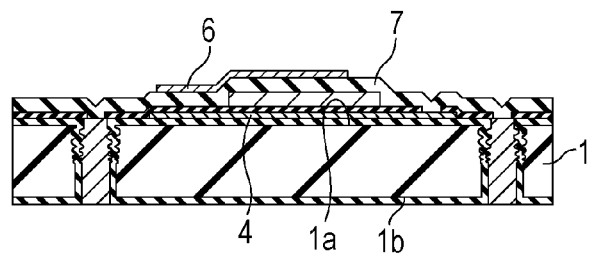
Figure 6G:
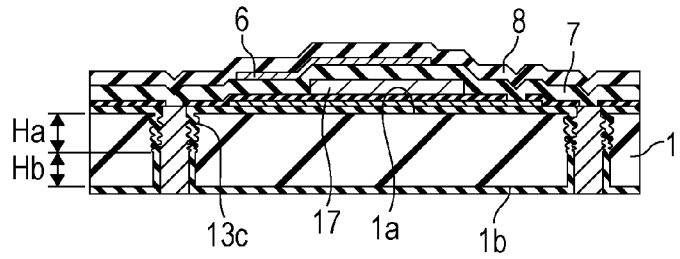
Figure 6H:
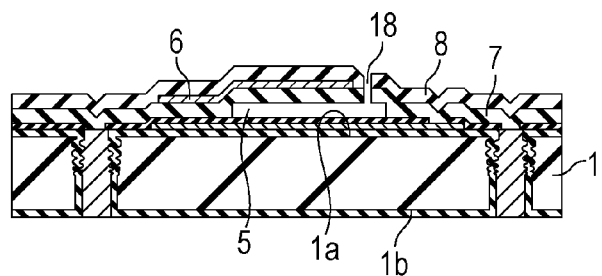
Figure 6I:
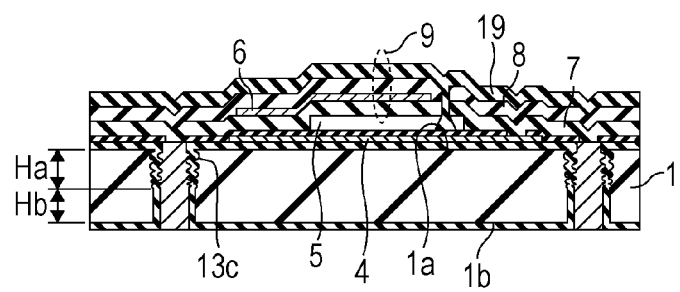
Figure 6J:
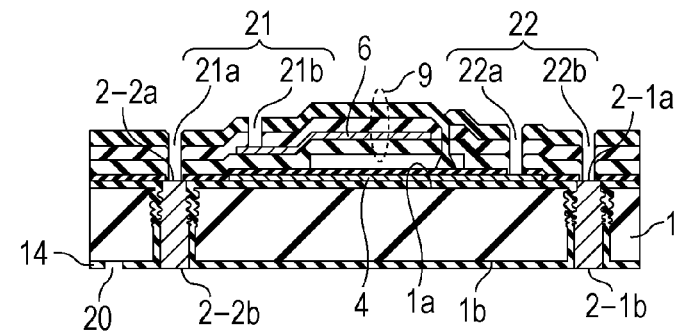
Figure 6K:
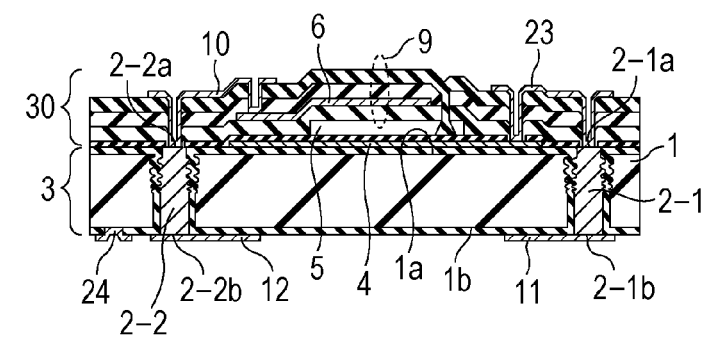

Regarding the CMUT of the present example, the element structure 30 is, as illustrated in FIG. 6K, formed on the first surface 1a of the through wiring substrate 3, and the electrode pads (including the electrode pads 11, 12, and 24) are formed on the second surface 1b of the through wiring substrate 3. The through wirings 2 (including the through wirings 2-1 and 2-2) are electrically connected to the element structure 30 on the first surface 1a side of the through wiring substrate 3 and connected to the electrode pads 11 and 12 on the second surface 1b side of the through wiring substrate 3. The element structure 30 includes the first electrode 4, the second electrode 6 separated from the first electrode 4 with a gap 5 formed therebetween, and the cell that includes a vibrating film 9 that includes the insulating films (including insulating films 7, 8, and 19) disposed on the upper and lower sides of the second electrode 6 and that can vibrate. The first electrode 4 is connected to the electrode pad 11 through the through wiring 2-1. The second electrode 6 is connected to the electrode pad 12 through the through wiring 2-2.

Initially, as illustrated in FIG. 6A, the through wiring substrate 3 is prepared. The through wiring substrate 3 is produced by the method according to the first example described with reference to FIGS. 3A to 3F. The first substrate 1 is an Si substrate. The first substrate 1 includes the first surface 1a and the second surface 1b. These two surfaces are mirror polished so as to have a surface roughness of Ra≤2 nm. The resistivity of the first substrate 1 is about 0.01 Ω·cm. The thickness of the first substrate 1 is about 300 µm. The through holes 13 each have a diameter of 50 µm. The through holes 13 are arranged with the period in the lateral direction set to 400 µm and the period in the longitudinal direction set to 2 mm. As the insulating film, the thermal oxidation film 14 formed of Si having a thickness of about 1 µm is formed in the inner wall of each of the through holes 13. Furthermore, the scalloped structure serving as the surface irregularities 13c is formed in each of the inner walls in the portion Ha on the first surface 1a side. The total length of the portion Ha is about 18 µm, an average interval of the scallops in the portion Ha is about 6 µm, and the maximum height of the scallops is about 5 µm. The scallops in the inner wall of the through hole 13 in the portion Hb on the second surface 1b side have a maximum height of 0.5 µm or smaller. The diameter of curvature of the envelope of the peaks (or troughs) of the surface irregularities 13c in the inner wall of the through hole 13 including the insulating film 14 is 5 µm or larger.

The through wirings 2 (including the through wirings 2-1 and 2-2) mainly formed of Cu are formed in the through holes 13 by electroplating. The end surfaces (including the end surfaces 2-1a, 2-1b, 2-2a, and 2-2b) of the through wirings 2 are planarized by the CMP process. After the planarization, on the first surface 1a side of the substrate, the levels of the end surfaces 2-1a and 2-2a of the through wirings 2 are the same or substantially the same as that of the surface of the thermal oxidation film 14 on the first surface 1a side. Furthermore, on the second surface 1b side, the levels of the end surfaces 2-1b and 2-2b of the through wirings 2 are the same or substantially the same as that of the surface of the thermal oxidation film 14 on the second surface 1b side. Two through wirings 2 are formed per element portion 32 (see FIG. 5) of the CMUT.

Next, as illustrated in FIG. 6B, the first electrode 4 is formed on the first surface 1a side of the first substrate 1. The first electrode 4 is one of the electrodes for driving the vibrating film 9 (see FIG. 6K). The first electrode 4, which is formed on the thermal oxidation film 14 formed of Si, is insulated from the first substrate 1. The first electrode 4 is positioned below a vibrating portion (a portion corresponding to the gap 5 of FIG. 6K) of the vibrating film 9 of the cell and extends from the vibrating portion to a region around the vibrating film 9. The first electrode 4 electrically connects the cells in the same element portion 32 to one another. The first electrode 4 is formed by stacking the Ti thin film having a thickness of about 10 nm and a W thin film having a thickness of about 50 nm. The first electrode 4 is formed by a method that includes deposition of metal, formation of an etching mask including photolithography, and etching of metal.

Next, as illustrated in FIG. 6C, a pattern of an insulating film 16 is formed. The insulating film 16 covers the surface of the first electrode 4. One of the functions of the insulating film 16 is that the insulating film 16 serves as an insulating and protective film for the first electrode 4. The insulating film 16 is a thin film of an Si oxide having a thickness of 200 nm. The Si-oxide thin film is formed by a chemical vapor deposition (CVD) method at the substrate temperature of about 300° C. After the deposition of the Si oxide has been performed, openings 16a, 16b, and 16c are formed in the insulating film 16. The openings 16a, 16b, and 16c are formed by a method that includes etching mask formation including photolithography and dry etching including reactive ion etching.

Next, as illustrated in FIG. 6D, a sacrificial layer 17 is formed. The sacrificial layer 17, which is for forming the gap 5 of the cell, is formed of Cr. The thickness and the shape of the sacrificial layer 17 are determined in accordance with required characteristics of the CMUT. Initially, a 200 nm thick Cr film is formed on the first surface 1a of the first substrate 1 by electron beam evaporation. Then, the Cr film is processed into a desired shape by a method including photolithography and wet etching. The sacrificial layer 17 has a cylindrical structure having a diameter of about 30 µm and a height of about 200 nm. A space occupied by the sacrificial layer 17 is to be connected to an etch hole 18 the formation of which will be described with reference to FIG. 6H.

Next, as illustrated in FIG. 6E, the insulating film 7 is formed. The insulating film 7 is to be in contact with the second electrode 6 the formation which is described with reference to FIG. 6F. One of the functions of the insulating film 7 is that the insulating film 7 serves as an insulating and protective film for the second electrode 6. The insulating film 7 is formed of Si nitride having a thickness of 400 nm. A thin film of the Si nitride is deposited by plasma enhanced chemical vapor deposition (PE-CVD) at the substrate temperature of about 300° C. During the deposition, the flow rate or the like of a deposition gas is controlled so that the Si nitride film which will become the insulating film 7 have tensile stress of about 0.1 GPa.

Next, as illustrated in FIG. 6F, the second electrode 6 is formed. The second electrode 6 is formed so as to face the first electrode 4 from above the first electrode 4. The second electrode 6 is one of the electrodes for driving the vibrating film 9. The second electrode 6 is formed by stacking a Ti film having a thickness of 10 nm and an AlNd alloy film having a thickness of 100 nm in this order. The second electrode 6 is formed by a method including sputter deposition of metal, formation of an etching mask including photolithography, and etching of metal. The deposition conditions are adjusted so that the second electrode 6 has tensile stress of 0.4 GPa or smaller when the manufacture of the CMUT is completed. The second electrode 6 electrically connects the cells in the same element portion 32 to one another.

Next, as illustrated in FIG. 6G, the insulating film 8 is formed. The insulating film 8 covers the upper surface of the second electrode 6. One of the functions of the insulating film 8 is that the insulating film 8 serves as an insulating and protective film for the second electrode 6. The insulating film 8 has a structure that is similar to or the same as that of the insulating film 7 and is formed by a method that is similar to or the same as that of the insulating film 7.

Next, as illustrated in FIG. 6H, the sacrificial layer 17 is removed by forming the etch hole 18. The etch hole 18 is formed by a method that includes photolithography and reactive ion etching. The sacrificial layer 17 (see FIG. 6G) of Cr is removed by introducing an etching liquid through the etch hole 18. Thus, the gap 5 having the same shape as that of the sacrificial layer 17 is formed.

Next, as illustrated in FIG. 6I, the thin film 19 is formed. The thin film 19 seals the etch hole 18 and is included in the vibrating film 9 together with the insulating film 7, the second electrode 6, and the insulating film 8 above the gap 5. The vibrating film 9 can vibrate. The thin film 19 is formed of Si nitride having a thickness of 800 nm. As is the case with the insulating film 7, the thin film 19 is deposited by PE-CVD at the substrate temperature of about 300° C. The entirety of the vibrating film 9 formed as described above has tensile stress of about 0.7 GPa and has a structure that is free from sticking or buckling and unlikely to be broken. The structure (including the material, thickness, and stress) of the vibrating film 9 is determined in the design in accordance with the required characteristics of the CMUT. The structure of the vibrating film 9 having been described here is only an example for describing the production method.

Next, as illustrated in FIG. 6J, contact holes 20, 21 (including contact holes 21a and 21b), and 22 (including contact holes 22a and 22b) for electrical connection are formed. The contact hole 20 is formed on the second surface 1b side of the first substrate 1 and serves as an opening that allows part of the second surface 1b to be exposed. The contact holes 21 and 22 are formed on the first surface 1a side of the first substrate 1. The contact hole 21a is an opening that allows part of the end surface 2-2a of the through wiring 2-2 to be exposed. The contact hole 21b is an opening that allows part of the surface of the second electrode 6 to be exposed. The contact hole 22a is an opening that allows part of the surface of the first electrode 4 to be exposed. The contact hole 22b is an opening that allows part of the end surface 2-1a of the through wiring 2-1 to be exposed. As the method of forming the contact hole 20, a method that includes the formation of an etching mask including photolithography and etching of an Si thermal oxide using buffered hydrogen fluoride (BHF) is used. As the method of forming the contact holes 21 and 22, a method that includes the formation of an etching mask including photolithography and reactive ion etching of an Si oxide is used. The contact holes 20, 21, and 22 have cylindrical shapes the diameter of which is, for example, about 10 μm.

Next, as illustrated in FIG. 6K, connecting wirings 10 and 23 and the electrode pads 11, 12, and 24 are formed. The connecting wirings 10 and 23 are each formed on the first surface 1a side of the first substrate 1 by stacking a Ti film having a thickness of about 10 nm and an Al film having a thickness of about 500 nm in this order. The connecting wiring 10 electrically connects the second electrode 6 and the end surface 2-2a of the through wiring 2-2 to each other through the contact holes 21 (including the contact holes 21a and 21b; see FIG. 6J). The connecting wiring 23 electrically connects the first electrode 4 and the end surface 2-1a of the through wiring 2-1 to each other through the contact holes 22 (including the contact holes 22a and 22b; see FIG. 6J). The electrode pads 11, 12, and 24 are formed on the second surface 1b side of the first substrate 1. The electrode pads 11, 12, and 24 are each formed of an Al film having a thickness of 500 nm. The electrode pads 11 and 12 are formed so as to be connected to the end surfaces 2-1b and 2-2b of the through wirings 2-1 and 2-2, respectively. As a result, the first electrode 4 disposed on the first surface 1a side of the first substrate 1 becomes electrically connectable on the second surface 1b side of the first substrate 1 through the through wiring 2-1. Likewise, the second electrode 6 disposed on the first surface 1a side of the first substrate 1 becomes electrically connectable on the second surface 1b side of the first substrate 1 through the through wiring 2-2. The electrode pad 24 is formed so as to be connected to the first substrate 1.

In order to improve a film-to-film adhesion property in the above-described steps of producing the insulating films 7, 8, and 9, plasma treatment may be performed on the surfaces of the underlying films before the deposition of the overlying films. By performing this plasma treatment, the surfaces of the underlying films are cleaned or activated.

Next, although it is not illustrated, the CMUT produced through the steps described with reference to FIGS. 6A to 6K is connected to the control circuit through the electrode pads 11, 12, and 24 by the ACF compression bonding method. At least one of the first electrode 4 and the second electrode 6 of each of the cells of each of the element portions 32 of the CMUT produced in the above-described production method is electrically connected. For driving, a bias voltage is applied to the first electrode 4, and the second electrode 6 is used as a signal application electrode or a signal extraction electrode. Signal noise can be reduced by grounding the first substrate 1 through the electrode pad 24. The highest temperature of the substrate is about 300° C. through the above-described steps described with reference to FIGS. 6A to 6K. With the present example, the effects that are the same as or similar to those obtained with the above-described embodiments and examples of the production method can be obtained.

Fourth Examples

Fourth examples, which are examples of application of the CMUT produced according to the third example, are described. The CMUT produced according to the third example can be used for any of an ultrasonograph utilizing an acoustic wave and a subject information acquisition apparatus such as a ultrasonic image forming apparatus. Subject information reflecting optical characteristic values of the subject including an optical absorption coefficient, subject information reflecting the difference in acoustic impedance, and so forth can be acquired by receiving an acoustic wave from a subject with the CMUT and in accordance with an output electrical signal.

Figure 7A:
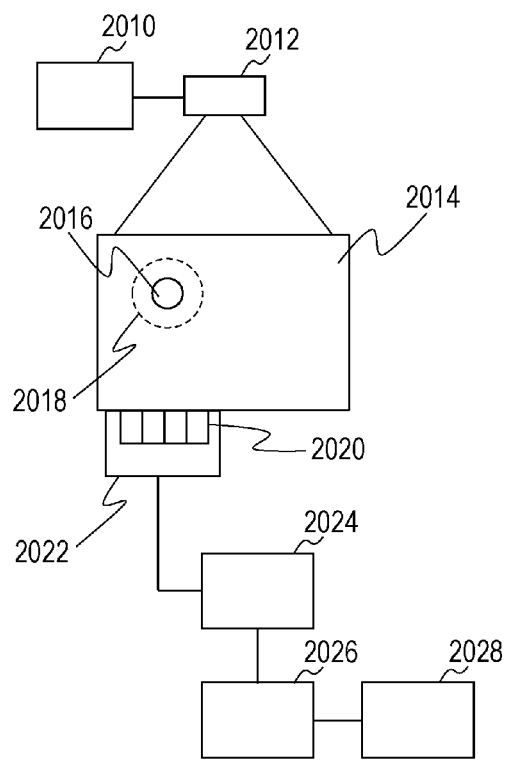
FIGS. 7A and 7B are block diagrams illustrating examples of application of the device according to one or more aspects of the present disclosure.

FIG. 7A illustrates an example of a subject information acquisition apparatus utilizing a photo-acoustic effect. Pulsed light emitted from a light source 2010 is radiated to a subject 2014 through an optical member 2012 including a lens, mirror, and an optical fiber. An optical absorption body 2016 existing in the subject 2014 absorbs energy of the pulsed light and generates an photo-acoustic wave 2018, which is an acoustic wave. A device 2020 disposed in a probe (search unit) 2022 includes an electromechanical transducer (CMUT) according to the present disclosure. The device 2020 receives a photo-acoustic wave 2018, converts the received photo-acoustic wave into an electrical signal, and outputs the electrical signal to a signal processing unit 2024. The signal processing unit 2024 performs signal processing such as analog-to-digital (AD) conversion and amplification on the received electrical signal and outputs the processed signal to a data processing unit 2026. The data processing unit 2026 acquires subject information (characteristic information reflecting optical characteristic values of the subject including an optical absorption coefficient) as image data in accordance with the received signal. Here, a processing unit includes the signal processing unit 2024 and the data processing unit 2026. The display 2028 displays an image in accordance with the image data received from the data processing unit 2026. As described above, the subject information acquisition apparatus according to the present example includes the device according to the present disclosure, the light source, and the processing unit. The device receives the photo-acoustic wave generated by radiating the light emitted from the light source to the subject and converts the received photo-acoustic wave into the electrical signal. The processing unit acquires the subject information in accordance with the electrical signal.

Figure 7B:
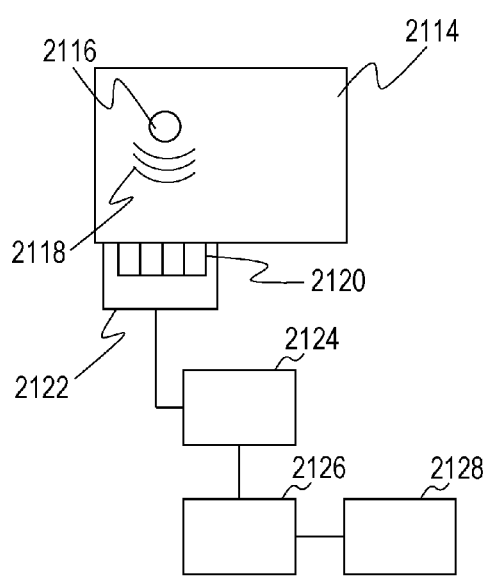

FIG. 7B illustrates a subject information acquisition apparatus such as an ultrasonic diagnostic apparatus utilizing reflection of an acoustic wave. A device 2120 that is disposed in a probe (search unit) 2122 and includes an electromechanical transducer (CMUT) according to the present disclosure transmits the acoustic wave to a subject 2114. The acoustic wave is reflected by a reflective body 2116. The device 2120 receives a reflected acoustic wave (reflected wave) 2118, converts the received acoustic wave into an electrical signal, and outputs the electrical signal to a signal processing unit 2124. The signal processing unit 2124 performs signal processing such as AD conversion and amplification on the received electrical signal and outputs the processed signal to a data processing unit 2126. The data processing unit 2126 acquires subject information (characteristic information reflecting the difference in optical impedance) as image data in accordance with the received signal. Here again, a processing unit includes the signal processing unit 2124 and the data processing unit 2126. A display 2128 displays an image in accordance with the image data received from the data processing unit 2126. As described above, the subject information acquisition apparatus according to the present example includes the device according to one or more aspects of the present disclosure and the processing unit that acquires the subject information in accordance with the electrical signal output from the device. The device receives the acoustic wave from the subject and outputs the electrical signal.

Scanning with the probe may be mechanically performed or manually performed by the user such as a doctor or a technician who moves the probe relative to the subject (hand-held type). Furthermore, in the case where the apparatus utilizes the reflected wave as illustrated in FIG. 7B, a probe that transmits the acoustic wave may be provided separately from a probe that receives the acoustic wave. Furthermore, the subject information acquisition apparatus may have the functions of both the apparatus of FIG. 7A and the apparatus of FIG. 7B so as to acquire both the subject information reflecting the optical characteristic values of the subject and the subject information reflecting the difference in acoustic impedance. In this case, the device 2020 of FIG. 7A may transmit the acoustic wave and receive the reflected wave in addition to the reception of the photo-acoustic wave. The CMUT as described above may be used also for a measurement device or the like that measures the magnitude of an external force. In this case, the magnitude of the external force applied to the surface of the CMUT is measured in accordance with an electrical signal from the CMUT that receives the external force.

While the present disclosure has been described with reference to exemplary embodiments, the scope of the following claims is to be accorded the broadest interpretation so as to encompass all such modifications and equivalent structures and functions.

This application claims the benefit of Japanese Patent Application No. 2015-243670, filed Dec. 15, 2015, which is hereby incorporated by reference herein in its entirety.

What is claimed is:

1. A method of producing a device in which an element structure is provided on a substrate including a through wiring, the method comprising the steps of:
   forming a through hole that extends from a first surface of the substrate to a second surface of the substrate disposed on an opposite side of the substrate to the first surface;
   forming the through wiring by filling the through hole with an electrically conductive material; and
   forming the element structure on a first surface side after the forming of the through wiring,
   wherein, in the step of forming the through hole, a degree of surface irregularities of an inner wall of the through hole is larger on the first surface side than on a second surface side.

2. The method according to claim 1,
   wherein, in the step of forming the through wiring, the electrically conductive material with which the through hole is filled is polished so as to form the through wiring.

3. The method according to claim 1,
   wherein the surface irregularities of the inner wall of the through hole include either or both of a surface undulating component having a long period and a surface roughness component having a short period.

4. The method according to claim 3,
   wherein, in the step of forming the through hole, the surface irregularities are formed such that the period of the surface undulating component of the surface irregularities is 5 μm or larger and the period of the surface roughness component of the surface irregularities is 5 μm or smaller.

5. The method according to claim 3,
   wherein, in the step of forming the through hole, the through hole is formed such that a maximum height of the surface undulating component of the surface irregularities of the inner wall of the through hole is in a range from 2 to 50 μm and a maximum height of the surface roughness component of the surface irregularities of the inner wall of the through hole is in a range from 0.1 to 5 μm.

6. The method according to claim 1,
   wherein, in the step of forming the through hole, the through hole is formed such that a portion of the inner wall of the through hole on the first surface side where the degree of the surface irregularities is larger has a depth from the first surface in a range from one to ten times a length of a period of the surface irregularities.

7. The method according to claim 1,
   wherein, in the step of forming the through hole, an insulating film is formed on surfaces of the substrate including the first surface, the second surface, and the inner wall of the through hole.

8. The method according to claim 1,
   wherein, in the step of forming the through hole, a diffusion preventing film that prevents metal diffusion is formed on the inner wall of the through hole.

9. The method according to claim 1,
   wherein, in the step of forming the through hole, a substance for a shape of irregularities is formed on the inner wall of the through hole so as to form the surface irregularities.

10. The method according to claim 1,
   wherein, in the step of forming the through hole, the surface irregularities of the inner wall of the through hole are formed at the same time as processing of the through hole.

11. The method according to claim 1,
wherein, in the step of forming the through hole, the inner wall of the through hole is smoothed.

12. The method according to claim 1,
wherein, in the step of forming the through wiring, the first surface of the substrate and a seed film formed on a seed substrate are bonded to each other with a bonding substance interposed therebetween, the bonding substance at a bottom portion of the through hole is removed so as to expose the seed film, and an inside of the through hole is filled with the electrically conductive material by electroplating starting from the exposed seed film.

13. The method according to claim 1,
wherein, in the step of forming the through wiring, the electrically conductive material is mainly formed of Cu.

14. The method according to claim 1,
wherein, in the step of forming the through wiring, one of end surfaces of the through wiring is planarized so as to be at the same level or substantially the same level as a level of the first surface of the substrate, and another end surface of the through wiring is planarized so as to be at the same level or substantially the same level as a level of the second surface of the substrate.

15. The method according to claim 1,
wherein, in the step of forming the through wiring, the electrically conductive material is polished by chemical mechanical polishing.

16. The method according to claim 1,
wherein in the step of forming the element structure on the first surface side, the element structure is a capacitive transducer or a piezoelectric transducer.

17. A method of producing a substrate including a through wiring, the method comprising the steps of:
forming a through hole that extends from a first surface of the substrate to a second surface of the substrate disposed on an opposite side of the substrate to the first surface; and
forming the through wiring by filling the through hole with an electrically conductive material,
wherein, in the step of forming the through hole, a degree of surface irregularities of an inner wall of the through hole is larger on a first surface side than on a second surface side.

18. A device in which an element structure is provided on a substrate including a through wiring,
wherein the device has a through hole that extends from a first surface of the substrate to a second surface of the substrate disposed on an opposite side of the substrate to the first surface,
wherein the device includes
the through wiring formed of an electrically conductive material with which an inside of the through hole is filled, and
the element structure provided on a first surface side, and
wherein a degree of surface irregularities of an inner wall of the through hole is larger on the first surface side than on a second surface side.

19. The device according to claim 18,
wherein, when a length of the through hole is H, the degree of the surface irregularities of the inner wall of the through hole is larger in a region having a length of 1/5H on the first surface side than in a region other than the region on the first surface side on the second surface side.

20. The device according to claim 19,
wherein the element structure is a capacitive transducer or a piezoelectric transducer.

21. A subject information acquisition apparatus comprising:
the device according to claim 20; and
a processing unit that acquires information about a subject in accordance with an electrical signal output from the device,
wherein the device receives an acoustic wave from the subject and converts the acoustic wave into the electrical signal.

22. The subject information acquisition apparatus according to claim 21, further comprising:
a light source,
wherein the device also receives a photo-acoustic wave generated by radiating light emitted from the light source to the subject and converts the photo-acoustic wave into an electrical signal, and
wherein the processing unit acquires the information about the subject in accordance with the electrical signal from the device.

23. A subject information acquisition apparatus comprising:
the device according to claim 20;
a light source; and
a processing unit that acquires information about a subject in accordance with an electrical signal output from the device,
wherein the device receives a photo-acoustic wave generated by radiating light emitted from the light source to the subject and converts the photo-acoustic wave into the electrical signal.

24. A device in which an element structure is provided on a substrate including a through wiring,
wherein the device has a through hole that extends from a first surface of the substrate to a second surface of the substrate disposed on an opposite side of the substrate to the first surface,
wherein the device includes
the through wiring formed of an electrically conductive material with which an inside of the through hole is filled, and
the element structure provided on a first surface side, and
wherein, when a length of the through hole is H, a degree of surface irregularities of an inner wall of the through hole is larger in a region having a length of 1/5H on the first surface side than in a region other than the region on the first surface side on a second surface side.

* * * * *